US010682377B2

(12) United States Patent
Solans et al.

(10) Patent No.: US 10,682,377 B2
(45) Date of Patent: Jun. 16, 2020

(54) **MUTANT *BORDETELLA* STRAINS AND METHODS OF USE**

(71) Applicants: Institut Pasteur de Lille, Lille (FR); Institut National de la Sante et de la Recherche Medicale (INSERM), Paris (FR)

(72) Inventors: Luis Solans, La Madeleine (FR); Camille Locht, Brussels (BE); Anne Tsicopoulos, Lille (FR); Saliha Ait-Yahia Sendid, La Madeleine (FR)

(73) Assignees: Institut Pasteur de Lille, Paris (FR); INSTITUT NATIONAL DE LA SANTÉET DE LA RECHERCHE MÉDICALE, Paris (FR)

( * ) Notice: Subject to any disclaimer, the term of this patent is extended or adjusted under 35 U.S.C. 154(b) by 108 days.

(21) Appl. No.: 15/472,436

(22) Filed: Mar. 29, 2017

(65) Prior Publication Data
US 2017/0283890 A1 Oct. 5, 2017

Related U.S. Application Data

(60) Provisional application No. 62/314,843, filed on Mar. 29, 2016.

(51) Int. Cl.
| | | |
|---|---|---|
| *A61K 39/02* | (2006.01) | |
| *A61K 35/74* | (2015.01) | |
| *A61K 39/00* | (2006.01) | |
| *A61K 9/00* | (2006.01) | |
| *A61K 35/00* | (2006.01) | |

(52) U.S. Cl.
CPC .............. *A61K 35/00* (2013.01); *A61K 9/007* (2013.01); *A61K 35/74* (2013.01); *A61K 39/099* (2013.01); *A61K 2039/522* (2013.01)

(58) Field of Classification Search
CPC .............. A61K 2039/522; A61K 35/74; A61K 39/099; A61K 9/007; A61K 35/00; A61K 9/00; A61K 2039/523; A61K 2039/543; A61K 2039/544; C12R 1/01
See application file for complete search history.

(56) References Cited

U.S. PATENT DOCUMENTS

| | | |
|---|---|---|
| 6,660,261 B1 | 12/2003 | Mielcarek |
| 6,713,072 B1 | 3/2004 | Pizza |
| 6,841,358 B1 | 1/2005 | Locht |
| 2005/0147607 A1 | 7/2005 | Reed |
| 2009/0246222 A1 | 10/2009 | Locht |
| 2010/0111996 A1 | 5/2010 | Leclerc |
| 2012/0121647 A1 | 5/2012 | Alonso |
| 2013/0183336 A1 | 7/2013 | Locht |

FOREIGN PATENT DOCUMENTS

| | | |
|---|---|---|
| EP | 2442826 | 4/2012 |
| FR | 2718750 | 10/1995 |
| WO | 9816553 | 4/1998 |
| WO | 03102170 | 12/2003 |
| WO | 2007104451 | 9/2007 |
| WO | 2008118592 | 10/2008 |
| WO | 2008156753 | 12/2008 |
| WO | 2010125014 | 11/2010 |
| WO | 2010146414 | 12/2010 |
| WO | 2013066272 | 5/2013 |
| WO | 2014060514 | 4/2014 |

OTHER PUBLICATIONS

Hegerle et al. Vaccine 32: 6597-6600, Epub Oct. 11, 2014.*
Srigley et al. Clin. Microbiol, Newsletter 37: 61-65, 2015.*
Locht, Camille, et al: "Common accessory genes for the Bordetella pertussis filamentous hemagglutinin and fimbriae share sequence similarities with the papC and papD gene families," The EMBO Journal, 1992, vol. 11(9):3175-3183.
Locht, Camille et al: "Bordetalla pertussis, molecular pathogenesis under multiple aspects," Current Opinion in Microbiology, 2001, vol. 4:82-89.
Kashimoto, Takashige, et al: "Identification of functional domains of Bordetella dermonecrotizing toxin," Infect. Immun., 1999, vol. 67(8):3727-3732.
Kavanagh, H. et al: "Attenuated bordetella pertussis vaccine strain BPZE1 modulates allergen-induced immunity and prevents allergic pulmonary pathology in a murine model," Clinical & Experimental Allergy, 2010, vol. 40(933-941.
Ho, Si Ying et al: "Highly attenuated Bordetella pertussis Strain BPZE1 as a potential live vehicle for delivery of heterologous vaccine candidates," Infection and Immunity, 2008, vol. 76:111-119.
Higgins, Sarah C. et al: "Toll-like receptor 4-mediated innate IL-10 activates antigen-specific regulatory T cells and confers resistance to Bordetella pertussis by inhibiting inflammatory pathology," The Journal of Immunology, 2003, vol. 171:3119-3127.
Feunou, Pascal et al: "Genetic stability of the live attenuated Bordetella pertussis vaccine candidate BPZE1," Vaccine, 2008, vol. 28:5722-5727.
Ennis, D.P. et al: "Prior Bordetella pertussis infection modulates allergen priming and the severity of airway pathology in a murine model of allergic asthma," Clin Exp Allergy, 2004, vol. 34:1488-1497.
Ennis, D.P. et al: Whole-cell pertussis vaccine protects against Bordetella pertussis exacerbation of allergic asthma, Immunology Letters 97, 2005, pp. 91-100.

(Continued)

*Primary Examiner* — Sarvamangala Devi
(74) *Attorney, Agent, or Firm* — Stanley A. Kim

(57) ABSTRACT

A method of reducing or preventing the development of airway inflammation in a subject includes the step of infecting the respiratory tract of a subject an amount of a composition including a pharmaceutically acceptable carrier and live attenuated pertactin-deficient *Bordetella* bacteria sufficient to colonize the respiratory tract of the subject. The step of infecting the subject with the live attenuated pertactin-deficient *Bordetella* bacteria results in reduction or prevention of the development of airway inflammation in the subject.

11 Claims, 12 Drawing Sheets

Specification includes a Sequence Listing.

(56) References Cited

OTHER PUBLICATIONS

Das, Pam: "Whopping cough makes global comeback," The Lancet Infectious Diseases, 2002, vol. 2:322.
Coppens, Isabelle et al: "Production of Neisseria meningitidis transferrin-binding protein B by recombinant Bordetella pertussis," Infection and Immunity, 2001, pp. 5440-5446.
Child Innovac; European Network on Nasal Vaccination against Respiratory Infections in Young Children, 2008, http://www.ist-world.org/ProjectDetails.aspx?; last accessed on Jan. 6, 2015.
Carbonetti, Nicholas H.: "Immunomodulation in the pathogenesis of Bordetella pertussis infection and disease," Current Opinion in Pharmacology, 2007, vol. 7:272-278.
Antoine, R. and C. Locht: "Roles of the disulfide bond and the carboxy-terminal region of the S1 subunit in the assembly and biosynthesis of pertussis toxin," Infect.Immun., 1990, vol. 56(6):1518-1526.
Alonso, Sylvie et al: "Production of nontypeable haemophilus influenzae HtrA by recombinant Bordetella pertussis with the use of filamentous hemagglutinin as a carrier," Infection and Immunity, 2005, pp. 4295-4301.
Abe, Takayuki et al: "Baculovirus induces an innate immune response and confers protection from lethal influenza virus infection in mice," J Immunol, 2003, vol. 171:1133-1139.
Feunou, Pascal et al: "Long-term immunity against pertussis induced by a single nasal administration of live attenuated B. pertussis BPZE1," Vaccine, 2010, vol. 28:7047-7053.
Mielcarek, Nathalie et al: "Dose Response of attenuated Bordetella pertussis BPZE1-induced protection in mice," Clinical and Vaccine Immunology, 2010, pp. 317-324.
Mielcarek, Nathalie et al: "Live attenuated B. pertussis as a single-dose nasal vaccine against whooping cough," PLoS Pathogens, 2006, vol. 2(7): 662-670.
Renauld-Mongenie, G. et al:Distinct roles of the N-terminal and C-terminal precursor domains in the biogenesis of the Bordetella pertussis filamentous hemagglutinin, J. Bacteriol., 1996, vol. 178(4):1053-1060.
Mattoo, S. et al: "Mechanisms of Bordetella pathogenesis," Frontiers in Bioscience, 2001, vol. 6:168-186.
Mattoo, S. and James D. Cherry: "Molecular pathogenesis, epidemiology, and clinical manifestations of respiratory infections due to Bordetella pertussis and other Bordetella subspecies," Clinical Microbiology Reviews, 2005, vol. 18(2):326-382.
Martignon, G. et al: "Does childhood immunization against infectious diseases protect from the development of atopic disease," Pediatr Allergy Immunol, 2005, vol. 16:193-200.
Locht, Camille et al: "Bordetella pertussis: from functional genomics to intranasal vaccination," Int. J. Med. Microbiol., 2004, vol. 293:583-588.
Harju, T.H. et al: Pathogenic bacteria and viruses in induced sputum or pharyngeal secretions of adults with stable asthma, Thorax, 2006, vol. 61:579-584.
Grueber, C. et al: "Early atopic disease and early childhood immunization—is there a link?," Allergy, 2008, vol. 63:1464-1472.
Gern, James E.: "Viral and bacterial infections in the development and progression of asthma," J Allergy Clin Immunol, 2000, pp. S497-S501.
Ennis, Darren P.: "A cellular pertussis vaccine protects against exacerbation of allergic asthma due to Bordetella pertussis in a murine model," Clin. Diagn. Lab. Immunol., 2005, vol. 12(3):409-417.
Kim, Young-Suk, et al.: "Inhibition of murine allergic airway disease by Bordetella pertussis," Immunology, 2004, vol. 112:624-630.
Li,R. et al: "Attenuated Bordetella pertussis BPZE1 protects against allergic airway inflammation and contact dermatitis in mouse models," Allergy, 2012, vol. 67:1250-1258.
Grueber, C. et al: "Common vaccine antigens inhibit allergen-induced sensitization and airway hyperresponsiveness in a murine model," Allergy, 2006, vol. 61:820-827.
Feunou, Pascal et al: "T- and B-Cell Mediated Protection Induced by Novel, Live, Attenuated Pertussis Vaccine in Mice. Cross Protection against Parapertussis," PLoS One, Apr. 2010, vol. 5, Issue 4:1-10.
Inatsuka, Carol S. et al: "Pertactin is required for Bordetella species to resist neutrophil-mediated clearance," Infection and Immunity, Jul. 2010, vol. 78, No. 7:2901-2909.
Solans, Luis et al: "The PhoP-dependent ncRNA Mcr7 modulates the TAT secretion system in *Mycobacterium tuberculosis*," PLOS, May 2014, vol. 10, No. 5:1-17.
Zeddeman, A. et al: "Investigations into the emergence of pertactin-deficient Bordetella pertussis isolates in six European countries, 1996 to 2012," Research Articles, Aug. 21, 2014, pp. 1-11; <<www.eurosurveillance.org.>>.
Thorstensson, R. et al: "A Phase I Clinical Study of a Live Attenuated Bordetella pertussis vaccine—BPZE1; A Single Centre, Double-Blind, Placebo-Controlled, Dose-Escalating Study of BPZE1 Given intranasally to healthy adult male volunteers," PLOS ONE, Jan. 2014, vol. 9, No. 1:10.
Yusibov, V. et al.: "Peptide-based candidate vaccine against respiratory syncytial virus," Vaccine, 2005, vol. 23:2261-2265.
Walker, K. E. et al.: "Characterizationof the dermonecrotic toxin in members of the genus *Bordetella*," Infect. Immun., 1994, vol. 62, No. 9:3817-3828.
Teman, UA. et al.: "A novel role for murine IL-4 in vivo: induction of MUC5AC gene expression and mucin hypersecretion," Am J Respir Cell Mol Biol., 1997, vol. 16(4):471-478.
Stith, Rebecca et al.: "The link between tracheal cytotoxin production and peptidoglycan recycling in Bordetella Pertussis," Abstracts of the General Meeting of the American Society for Microbiology, New Orleans; 1996; vol. 96:184 (XP008013937).
Li, Rui, et. al.: "Attenuated Bordetella pertussis BPZE1 as a live vehicle for heterologous vaccine antigens delivery thorugh the nasal route," Bioengineered Bugs, 2011, vol. 2(6):315-319.
Li, Rui, et al.: "Development of live attenuated Bordetella pertussis strains expressing the universal influenza vaccine candidate M2e," Vaccine, 2011, vol. 29:L5502-5511.
Romagnani, Sergio, "Immunologic influences on allergy and the TH1/TH2 balance," J Allergy Clin Immunol, 2004, pp. 395-400.
Nemery, B. et al.: "Interstitial lung disease induced by exogenous agents: factors governing susceptibility," Eur Respir J, 2001, vol. 18, Suppl. 32:30s-42s.
Neirynck, Sabine, et al.: "A universal influenza A vaccine based on the extracellular domain of the M2 protein," Nature Medicine, 1999, vol. 5:1157-1163.
Nagel, Gabriele et al.: "Association of pertussis and measles infections and immunizations with asthma and allergic sensitization in ISAAC Phase Two," Pediatric Allergy and Immunology, 2012, vol. 23:736-745.
Morokata, T. et al.: "C57BL/6 mice are more susceptible to antigen-induced pulmonary eosinophilia than BALB/c mice, irrespective of systemic T helper 1/T helper 2 responses," Immunology, 1999, vol. 98:345-351.
Mielcarek, Nathalie et al.: "Homologous and heterologous protection after single intranasal administration of live attenuated recombinant Bordetella pertussis," Nature Biotechnology, 1998, vol. 16:454-457.
Marsland, B.J., et al.: "Allergic airway inflammation is exacerbated during acute influenza infection and correlates with increased allergen presentation and recruitment of allergen-specific T-helper type 2 cells," Clinical & Experimental Allergy, 2004, vol. 34, Issue 8.
Mahon, B., et al.: "Atypical Disease after Bordetella pertussis Respiratory Infection of Mice with Targeted Disruptions of Interferon-γ Receptor or Immunoglobulin μ Chain Genes," J. Exp. Med., 1997, vol. 186, No. 11:1843-1851.
Locht, Camille, et al.: "Bordetella pertussis: from functional genomics to intranasal vaccination," Iny. J. Med. Microbiol., 2004, vol. 293:583-588.
Li, Z.M., et al.: "Cloning and sequencing of the structural gene for the porin protein of Bordetella pertussis," Molecular Biology, 1991, vol. 5 (7):1649-1656.

(56) References Cited

OTHER PUBLICATIONS

De Filette et al.: "Improved design and intranasal delivery of an M2e-based human influenza A vaccine," Vaccine, 2006, vol. 24, pp. 6597-6691.
Laemmli, U.K.: "Cleavage of Structural Proteins during the Assembly of the Head of Bacteriophage T4," Nature, 1970, pp. 680-685.
Humbert, Marc et al.: "Elevated expression of messenger ribonucleic acid encoding IL-13 in the bronchial mucosa of atopic and nonatopic subjects with asthma," Journal of Allergy and Clinical Immunology, 1997, vol. 99 (5):657-665.
Huang, Chin Chiang, et al.: "Experimental Whooping Cough," N Engl J Med, 1962, vol. 266:105-111.
Holgate, Stephen, et al.: "The anti-inflammatory effects of omalizumab confirm the central role of IgE in allergic inflammation," J Allergy Clin Immunol, 2005, vol. 115:459-465.
Hausman, Sally Z. and Burns, Drusilla L.: "Use of Pertussis Toxin Encoded by ptx Genes from Bordetella bronchiseptica to Model the Effects of Antigenic Drift of Pertussis Toxin on Antibody Neutralization,".
Hansen, Gesine et al.: "Allergen-specific Th1 cells fail to counterbalance Th2 cell-induced airway hyperreactivity but cause severe airway inflammation," J. Clin. Invest, 1999, vol. 103:175-183.
Hamelmann, E. et al.: "Role of IgE in the development of allergic airway inflammation and airway hyperresponsiveness a murine model," Allergy, 1999, vol. 54:297-305.
Gleich, Gerald J.: "Mechanisms of eosinophil-associated inflammation," J. Allergy Clin. Immunol., 2000, pp. 651-663.
Giefing, Carmen et al.: "Discovery of a novel class of highly conserved vaccine antigens using genomic scale antigenic fingerprinting of pneumococcus with human antibodies," JEM, 2008, vol. 205(1):117-131.
Galli, Stephen J., et al.: "The development of allergic inflammation," Nature, 2008, vol. 454:445-454.
Zhao, Zhanqin, et al.: "Protecting mice from fatal Bordetella brochiseptica infection by immunization with recombinant pertactin antigens, " Acta Microbiologica Sinica, 2008, vol. 48 (3):337-341.
Willems, Rob J.L. et al.: "The efficacy of a whole cell pertussis vaccine and fimbriae against Bordetella pertussis and Bordetella parapertussis infections in a respiratory mouse model," Vaccine, 1998, vol. 16 (4)410-416.
Varga, Steven M. et al: "The Attachment (G) Glycoprotein of Respiratory Syncytial Virus Contains a Single Immunodominant Epitope That Elicits Both Th1 and Th2 CD4+ T Responses," The Journal of Immunology, 2000, vol. 165:6487-6495.
Stibitz, Scott: "Use of conditionally counterselectable suicide vectors for allelic exchange," Methods in Enzymology, 1994, vol. 235:458-465; Abstract.
Stainer, D.W. and M.J. Scholte: "A simple chemically defined medium for the production of phase I Bordetella pertussis," Journal of General Microbiology, 1971, vol. 63:211-220.
Skerry, Ciaran M. and Bernard P. Mahon: "A live, attenuated bordetella pertussis vaccine provides long-term protection against virulent challenge in a murine model," Clinical and Vaccine Immunology, 2011, vol. 18:187-193.
Simon, R. et al: "A broad host range mobilization system for in vivo genetic engineering: transposon mutagenesis in gram negative bacteria," Nature Biotechnology, 1983, vol. 1:784-791.
Reveneau, Nathalie et al: "Tetanus toxin fragment C-specific priming by intranasal infection with recombinant Bordetella pertussis," Vaccine, 2002, vol. 20:926-933.
Renauld-Mongenie, Genevieve, et al: "Induction of mucosal immune responses against a heterologous antigen fused to filamentous hemagglutinin after intranasal immunization with recombinant Bordetella pertussis," Proc. Natl. Acad. Sci., 1996, vol. 93:7944-7949.
Quandt, J. and Michael F. Hynes: "Versatile suicide vectors which allow direct selection for gene replacement in gram-negative bacteria," Gene, 1993, vol. 127 (1):15-21; Abstract.
Power, Ultan F. et al: "Identification and characterisation of multiple linear B cell protectopes in the respiratory syncytial virus G protein," Vaccine, 2001, vol. 19, Issues 17-19:2345-2351; Abstract.
Feunou, Pascal: "T.119.T-but not B-cell-mediated protection induced by nasal administration using live attenuated bordetella pertussis BPZE1 Cross Protect Against B. Parapertussis," Clinical Immunology, 2009, vol. 131, Supplement 1, p. S86; Abstract.
Narasaraju, T. et al: "Adaptation of human influenza H3N2 virus in a mouse peumonitis model: insights into viral virulence, tissue tropism and host pathogenesis," Microbes and Infection 11, 2009:2-11.
Mutsch, M. et al: Use of the inactivated intranasal influenza vaccine and the risk of Bell's Palsy in Switzerland, The New England Journal of Medicine, 2004, vol. 350:896-903.
Mills, KH et al: "A respiratory challenge model for infection with Bordetella pertussis application in the assessment of pertussis vaccine potency and in defining the mechanism of protective immunity," Dev Biol Stand, 1998, vol. 95:31-41; Abstract.
Mielcarek, Nathalie et al: "Attenuated bordetella pertussis: new live vaccines for intranasal immunisation," Vaccine, 2006, S2:54-55.
Mielcarek, Nathalie et al: "Intranasal priming with recombinant Bordetella pertussis for the induction of a systemic immune response against a heterologous antigen," Infection and Immunity, 1997:544-550.
Mielcarek, Nathalie et al: "Nasal vaccination using live bacterial vectors," Advanced Drug Delivery Review, 2001, vol. 51:55-69.
Mekseepralard, C. et al: "Protection of mice against human respiratory syncytial virus by wild-type and aglycosyl mouse-human chimaeric IgG antibodies to subgroup-conserved epitopes on the G glycoprotein," Journal of General Virology, 2006, vol. 87:1267-1273.
Menozzi, F.D. et al: "Identification and purification of transferring- and lactoferrin-binding proteins of bordetella pertussis and bordetella bronchiseptica," Infection and Immunity, 1991:3982-3988.
McGuirk, P. et al: Pathogen-specific T regulatory 1 cells induced in the respiratory tract by a bacterial molecule that stimulates interleukin 10 production by dendritic cells: a novel strategy for evasion of protective T helper type 1 resonses by Bordella pertussis.
Mascart, Francoise, et al: "Bordetella pertussis infection in 2-month-old infants promotes type 1 T cell responses," The Journal of Immunology, 2003, vol. 170:1504-1509.
Marsolais, David et al: "A critical role for the sphingosine analog AAL-R in dampening the cytokin response during infuenza virus infection," The National Academy of Sciences of the USA, 2009, vol. 106(5):1560-1565.
Stevenson, Andrew and Mark Roberts, "Use of bordetella bronchiseptica and bordetella pertussis as live vaccines and vectors for heterologous antigens," FEMS Immunology and Medical Microbiology, 2003, vol. 37:121-128.
Li, Rui: "Development of Bordetella Pertussis as a live vehicle for heterologous antigen delivery, and its application as a universal influenza A vaccine," Thesis, National University of Singapore, 2010.
Burnette, W. Neal et al.: "Pertussis Toxin S1 Mutant with Reduced Enzyme Activity and a Conserved Protective Epitope," Science, Nov. 1988, vol. 242 (4875): 72-74.
Gross, Mary K. et al: "Targeted mutations that ablate either the adenylate cyclase or hemolysin function of the bifunctional cyaA toxin of Bordetella pertussis abolish virulence," Proc. Natl. Acad. Sci. USA, Jun. 1992, vol. 89: 4898-4902.
Lim, Annabelle et al.: "Protective role of adenylate cyclase in the context of a live pertussis vaccine candidate," Microbes and Infection, 2014, vol. 16:51-60.
Wang, Xianzhe and Jennifer A. Maynard: "The Bordetella Adenylate cyclase repeat-in-toxin (RTX) domain is immunodominant and elicits neutralizing antibodies," The Journal of Biological Chemistry, 2015, vol. 290, No. 6:3576-3591.

* cited by examiner

BPZE1P construction PCR

*prn* UPg PCR

*prn* LOg PCR

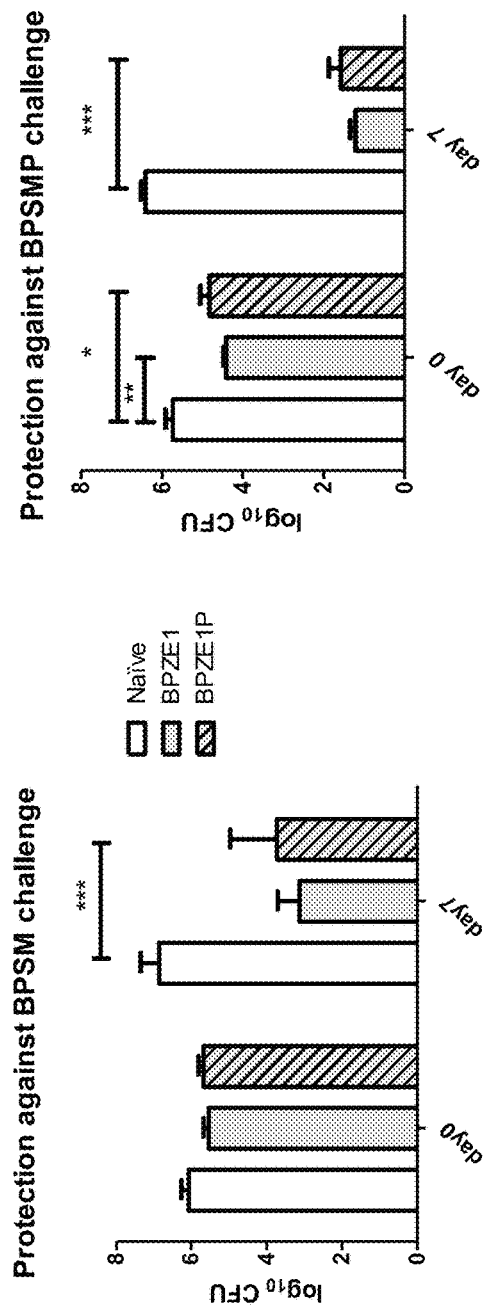
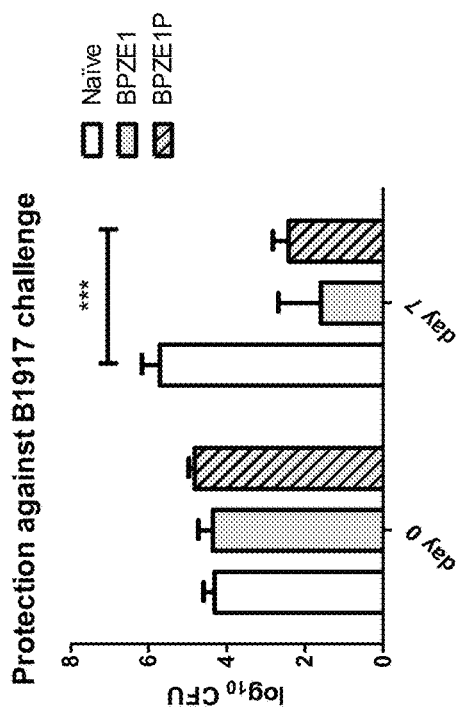
FIG. 4A
FIG. 4B
FIG. 4C

MUTANT BORDETELLA STRAINS AND METHODS OF USE

CROSS-REFERENCE TO RELATED APPLICATIONS

The present application claims the priority of U.S. provisional patent application Ser. No. 62/314,843 filed on Mar. 29, 2016.

SEQUENCE LISTING

The instant application contains a Sequence Listing which has been filed electronically in ASCII format and is hereby incorporated by reference in its entirety. Said ASCII copy, created on Mar. 27, 2017, is named 7056-0074_SL.txt and is 2,134 bytes in size

STATEMENT AS TO FEDERALLY SPONSORED RESEARCH

Not applicable.

FIELD OF THE INVENTION

The invention relates generally to the fields of microbiology, immunology, allergy, and medicine. More particularly, the invention relates to live attenuated *Bordetella pertussis* strains deficient in pertactin, and their use as prophylactic and therapeutic agents in various disease settings.

BACKGROUND

Microbial organisms and their components have long been known to affect the immune systems of mammals. Infection with virulent bacteria and viruses can cause severe illness or death. Contributing toward this, purified components of bacteria and viruses can also cause pathology by inducing inflammatory responses or otherwise causing the immune system to behave in an undesirable manner. Despite this, vaccines including whole bacteria, viruses, or parts thereof have not only proven to be one of the most powerful tools that medicine has developed to prevent serious infections, but also can cause other beneficial effects. For example, in experimental models, a live attenuated pertussis vaccine candidate named BPZE1 (see WO2007104451A1) was found to not only protect against virulent *Bordetella pertussis*, but also to exert potent anti-allergic and anti-asthma effects by dampening hyperimmune responses to allergens (see WO2013066272A1).

Developing safe and effective vaccines nonetheless remains challenging for several reasons. Among these, despite modern molecular biology techniques and significant advances in our understanding of microbiology and immunology, it remains quite difficult to produce a vaccine product that is sufficiently attenuated to not cause significant pathology, while at the same time sufficiently immunogenic to induce an effective and long-lasting immune response against the target pathogen. In the case of live attenuated whole-cell bacterial vaccines, arriving at an optimal level of attenuation is particularly troublesome because overattenuation by reducing the amount or activity of virulence factors can result in a vaccine that is poorly immunogenic and/or unable to survive or replicate in a subject for a sufficient time after administration to induce an immune response.

SUMMARY

Described herein is the development of pertactin-deficient *Bordetella* strains, and their use in inducing protective immune responses against pathologic *Bordetella* infection as well as in treating or preventing respiratory tract inflammation such as that observed in allergic asthma. Pertactin, an outer membrane protein of *Bordetella* bacteria, serves as a virulence factor by promoting adhesion to a variety of cells. In the experiments described below, it was discovered that a pertactin-deficient mutant of BPZE1, termed BPZE1P (deposited in accordance with the requirements of the Budapest Treaty with the Collection Nationale de Cultures de Microorganismes ("CNCM"), 25, Rue du Docteur Roux, Paris Cedex 15, 75724, France on Dec. 12, 2016 under accession number CNCM-I-5150), was able to colonize the respiratory tract, induce antibody responses against *Bordetella*, and protect against and treat allergic lung disease. The discovery was surprising because as others have shown that pertactin was required for *Bordetella* to resist neutrophil-mediated clearance, *B. pertussis* deficient in this virulence factor would have been expected to be cleared too rapidly to allow the induction of a protective immune responses. See, Inatsuka et al. Infect. Immun. 2010; 78: 2901-2909.

In the absence of anti-pertactin antibodies, BPZE1P colonized lungs as efficiently as BPZE1 and induced protective immunity against *B. pertussis* challenge as efficiently as BPZE1. In the presence of anti-pertactin antibodies, BPZE1P colonized the mouse lungs significantly better than BPZE1. Therefore, pertactin-deficient *B. pertussis* strains such as BPZE1P may be advantageous in protecting against respiratory tract inflammation in subjects with high pre-existing titers of pertactin antibodies, including those previously vaccinated with pertactin-containing acellular vaccines.

Accordingly described herein are methods of reducing or preventing the development of airway inflammation in a subject by administering to the respiratory tract of the subject an amount of a composition including a pharmaceutically acceptable carrier and live pertactin-deficient *Bordetella* bacteria sufficient to colonize the respiratory tract of the subject and thereby reduce or prevent the development of airway inflammation in the subject. In these methods, the airway inflammation can be associated with one or more of airway resistance, eosinophil infiltration in the lungs of the subject, and/or increased amounts of inflammatory cytokines in the lungs of the subject. Colonization of the respiratory tract of the subject can result in reduction or prevention of such airway resistance, eosinophil infiltration, and/or increased amounts of inflammatory cytokines.

Also described herein are compositions including a pharmaceutically acceptable carrier and live pertactin-deficient *Bordetella* bacteria capable of colonizing the respiratory tract of a subject and reducing or preventing the development of airway inflammation in the subject.

In the methods and compositions described herein, the live pertactin-deficient *Bordetella* bacteria can lack a functional gene encoding pertactin, also be deficient in tracheal cytotoxin (TCT), *pertussis* toxin (PTX), and/or dermonecrotic toxin (DNT). The live pertactin-deficient *Bordetella* bacteria can be BPZE1P. The airway inflammation can be caused by exposure to an allergen, and the subject can be one diagnosed with asthma, interstitial lung disease, or allergic rhinitis; one having greater than 10 ng per ml of anti-pertactin antibodies in its serum; or one that has previously been immunized with a vaccine containing pertactin or a pertactin-like antigen.

As used herein, "pertactin" is the outer surface membrane protein produced by *Bordetella pertussis* and its close relatives, such as *Bordetella parapertussis* that is involved in the binding of *Bordetella* bacteria to host cells as described in Leininger et al., *Proc. Nat'l. Acad. Sci. USA*, 1991, 88:345-9. Conserved regions in this protein, such as its passenger and autotransporter domains, contribute directly to the overall virulence and pathogenicity of these organisms.

As used herein, the abbreviation "PTX" refers to pertussis toxin, a major virulence factor of *B. pertussis*, which induces metabolic changes and alters immune responses in the host as described in Saukkonen et al., *Proc. Natl. Acad. Sci. USA.*, 1992, 89:118-122.

As used herein the abbreviation "DNT" refers to pertussis dermonecrotic toxin (also called lethal toxin), a toxin found in *B. pertussis* which induces inflammation, vasoconstriction and dermonecrotic lesions in sites where *B. pertussis* colonize the respiratory tract. See Fukui-Miyazaki et al., *BMC Microbiol.* 2010, 10:247.

As used herein the abbreviation "TCT" refers to tracheal cytotoxin, a disaccharide tetrapeptide derivative of peptidoglycan synthesized by bordetellae, which induces the production of interleukin-1 and nitric oxide synthase, and causes stasis of cilia and lethal effects on respiratory epithelial cells. See Luker et al., *Proc. Natl. Acad. Sci. USA.*, 1993, 90, 2365-2369

As used herein, a "pertactin-deficient" *Bordetella* strain is one that exhibits at least less than 50% (e.g., less than 50, 40, 30, 20, 10, 5, 4, 3, 2, or 1%) of the pertactin activity found in BPZE1 under the conditions described in the Examples section below, one that exhibits no detectable pertactin activity, or one that exhibits not detectable expression of pertactin as determined by Western blotting.

The term "functional" when referring to a toxin or virulence factor in a bacterial strain means that (i) the toxin/virulence factor expressed by the strain has not been mutated to eliminate or at least reduce by greater than 50% its enzymatic activity compared to the non-mutated version of the toxin/factor, and/or (ii) that a bacterial strain expressing the toxin/factor has not been engineered or selected to eliminate or at least reduce by greater than 50% the number of molecules of that toxin/factor compared to the starting strain from which the engineered or selected strain was derived.

The term "mammal", "mammalian subject" or "subject" encompasses any of various warm-blooded vertebrate animals of the class Mammalia, including human beings.

Unless otherwise defined, all technical terms used herein have the same meaning as commonly understood by one of ordinary skill in the art to which this invention belongs. Methods and materials similar or equivalent to those described herein can be used in the practice or testing of the present invention. All publications, patents, and patent applications mentioned herein are incorporated by reference in their entirety. In the case of conflict, the present specification, including definitions will control. In addition, the particular embodiments discussed below are illustrative only and not intended to be limiting.

DESCRIPTION OF THE DRAWINGS

FIG. 4A is a graph showing BPZE1- and BPZE1P-mediated protection in Balb/c mice challenged intranasally with $10^6$ viable *B. pertussis* bacteria of the BPSM strain.

FIG. 4B is a graph showing BPZE1- and BPZE1P-mediated protection in Balb/c mice challenged intranasally with $10^6$ viable *B. pertussis* bacteria of the BPSMP strain.

FIG. 4C is a graph showing BPZE1- and BPZE1P-mediated protection in Balb/c mice challenged intranasally with $10^6$ viable *B. pertussis* bacteria of the B1917 strain.

DETAILED DESCRIPTION

Figure 1:
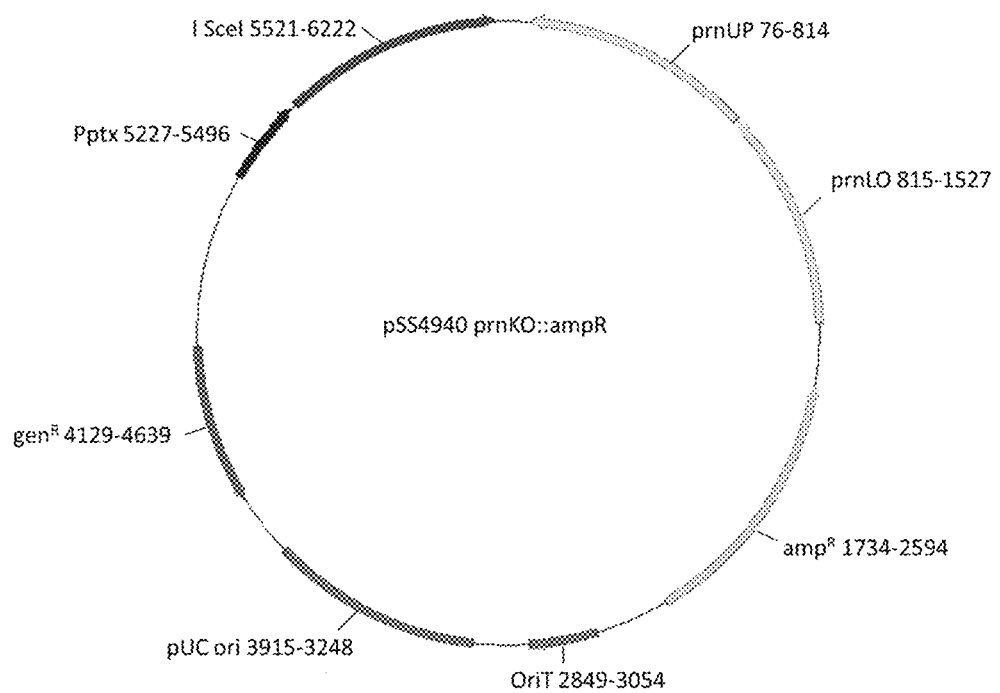
FIG. 1A is a diagram showing the structure of a plasmid used in the construction of BPZE1P.
FIG. 1B is another diagram showing the construction of BPZE1P, and photographs of gels showing the results of PCR amplification of the prn UPg and prn Log fragments.
FIG. 1C is photographs of immunoblots showing the presence of pertactin in BPZE1, but not in BPZE1P lysates and supernatants.

Described herein are *Bordetella* strains deficient in pertactin and their use in stimulating anti-*Bordetella* immune responses as well as in preventing and treating respiratory tract inflammation. The below described embodiments illustrate representative examples of these methods. Nonetheless, from the description of these embodiments, other aspects of the invention can be made and/or practiced based on the description provided below.

General Methodology

Methods involving conventional microbiological, immunological, molecular biological, and medical techniques are described herein. Microbiological methods are described in Methods for General and Molecular Microbiology (3d Ed), Reddy et al., ed., ASM Press. Immunological methods are generally known in the art and described in methodology treatises such as Current Protocols in Immunology, Coligan et al., ed., John Wiley & Sons, New York. Techniques of molecular biology are described in detail in treatises such as Molecular Cloning: A Laboratory Manual, 2nd ed., vol. 1-3, Sambrook et al., ed., Cold Spring Harbor Laboratory Press, Cold Spring Harbor, N.Y., 2001; and Current Protocols in Molecular Biology, Ausubel et al., ed., Greene Publishing and Wiley-Interscience, New York. General methods of medical treatment are described in McPhee and Papadakis, Current Medical Diagnosis and Treatment 2010, 49th Edition, McGraw-Hill Medical, 2010; and Fauci et al., Harrison's Principles of Internal Medicine, 17th Edition, McGraw-Hill Professional, 2008.

Pertactin-Deficient *Bordetella* Strains

*Bordetella* species such as *Bordetella pertussis*, *Bordetella parapertussis*, and *Bordetella bronchiseptica* that are deficient in pertactin expression (e.g., those that express at least 50, 60, 70, 80, 90, 95, 96, 97, 98, or 99% less pertactin than do corresponding strains) can be used to generate immune responses against *Bordetella* species, as well as to treat and/or prevent respiratory tract inflammation such as that which occurs in allergic asthma. Live, attenuated, pertactin-deficient *Bordetella pertussis* and live, attenuated, pertactin-deficient *Bordetella parapertussis* are preferred for use for treating or preventing allergic respiratory tract inflammation in human subjects. The live attenuated pertactin-deficient *Bordetella* strains described herein can be made by adapting methods known in the art such as those described in the Examples section below. The starting strain can be any suitable *Bordetella* species. Examples of *Bordetella* species include *B. pertussis*, *B. parapertussis*, and *B. bronchiseptica*. *B. pertussis* is preferred for use as the starting strain for vaccines and methods for preventing pertussis infection. Several suitable *Bordetella* strains for use as starting strains are available from established culture collections (e.g., the American Type Culture Collection in Manassas, Va.) or can be isolated from natural reservoirs (e.g., a patient having pertussis) by known techniques (e.g., as described in Aoyama et al., Dev. Biol. Stand, 73:185-92, 1991).

*Bordetella* strains which express functional pertactin can be made deficient in this molecule or its activity by selection or, preferably for stability purposes, mutagenesis (e.g., deletion of the native prn gene as described below). Alternatively, *Bordetella* species deficient in pertactin can also be isolated from natural sources (e.g., human subjects or other mammals infected or colonized with such strains). Because insufficient attenuation of a pathogenic strain of *Bordetella* might cause a pathological infection in a subject, it is preferred that the pertactin-deficient *Bordetella* strain used also have lower levels of other functional virulence factors. On the other hand, to ensure that the pertactin-deficient *Bordetella* strain retains the ability to colonize a subject and exert a protective effect on respiratory tract inflammation, it must not be overly attenuated. Attenuation might be achieved by mutating the strain to reduce its expression of pertactin and one or more (e.g., 1, 2, 3, 4, 5 or more) of the following: pertussis toxin (PTX), dermonecrotic toxin (DNT), tracheal cytotoxin (TCT), adenylate cyclase (AC), lipopolysaccharide (LPS), filamentous hemagglutinin (FHA), or any of the bvg-regulated components. Attenuation might also be achieved by mutating the strain to reduce the biological activity of pertactin and one or more (e.g., 1, 2, 3, 4, 5 or more) of the following: pertussis toxin (PTX), dermonecrotic toxin (DNT), tracheal cytotoxin (TCT), adenylate cyclase (AC), lipopolysaccharide (LPS), filamentous hemagglutinin (FHA), or any of the bvg-regulated components. Examples of methods for making such mutants are described herein and in U.S. Pat. No. 9,119,804. In the experiments presented below, a *Bordetella* strain deficient in functional pertactin, functional PTX, functional DNT, and functional TCT was able to colonize the respiratory tract of subjects, induce immune responses against *Bordetella*, and reduce or prevent the development of allergic and inflammatory responses. Accordingly, *Bordetella* strains, such as BPZE1P, which are deficient in these four virulence factors and can colonize a subject and induce immune responses targeting *Bordetella* strains and/or reduce or prevent the development of allergic and inflammatory responses are preferred.

A variety of methods are known in the art for attenuating an infectious bacterial strain. These include passaging the strain in vitro until virulence is lost, non-specific chemical mutagenesis followed by screening and selection based on phenotype, and using targeted molecular biology techniques such as those described in the Examples section below (including allelic exchange) and in Methods for General and Molecular Microbiology (3d Ed), Reddy et al., ed., ASM Press. Using these methods, the genes encoding pertactin, PTX, and/or DNT can be deleted or mutated to an enzymatically inactive form (which is preferred where it is desired to retain the toxin's antigenicity). TCT production can be significantly (e.g., >than 99.99, 99.90, 99.8, 99.7, 99.6, 99.5, 99.0, 98, 97, 96, 95, or 90%) reduced by replacing the native ampG gene (unlike other species, *B. pertussis* ampG does not actively recycle TCT-containing peptidoglycan) with a heterologous (e.g., from *E. coli* or another gram-negative species) ampG gene, or by mutating the native ampG gene such that it is active at recycling peptidoglycan.

Modification of a starting strain to reduce or remove toxin/virulence factor activity can be confirmed by sequencing the genomic DNA or genes encoding the toxins of the modified strains. Southern, Northern, and/or Western blotting might also be used to confirm that the target genes have been deleted or that expression of the target factors has been reduced or removed. Biological activity can also be evaluated to confirm reduction or removal of toxin/virulence factor activity. Once the modifications have been confirmed, the modified strains can be tested for the ability to colonize a subject and to induce protective immunity against *Bordetella* infection or to reduce or prevent the development of allergic and inflammatory responses by known methods such as those described in the Examples section below.

Compositions for Modulating Immune Responses

The live attenuated *Bordetella* strains described herein can be used in compositions that protect a mammalian subject from developing a *Bordetella* infection (e.g., pertussis), or to reduce the symptoms of such an infection. They can also be used to reduce or prevent the development of allergic and inflammatory responses in a subject such as asthma, allergic rhinitis, interstitial lung disease, food allergies, peanut allergy, venom allergies, atopic dermatitis, contact hypersensitivity, and anaphylaxis. For use in therapeutic or prophylactic compositions, the live attenuated *Bordetella* strains are typically formulated with a pharmaceutically acceptable excipient. Examples of pharmaceutically acceptable excipients include, e.g., buffered saline solutions, distilled water, emulsions such as an oil/water emulsion, various types of wetting agents, sterile solutions, and the like.

The vaccines can be packaged in unit dosage form for convenient administration to a subject. For example, a single dose of between $1 \times 10^4$ to $1 \times 10^9$ (e.g., $1 \times 10^4$, $5 \times 10^4$, $1 \times 10^5$, $5 \times 10^5$, $1 \times 10^6$, $5 \times 10^6$, $1 \times 10$, $5 \times 10^7$, $1 \times 10^8$, $5 \times 10^8$, or $1 \times 10^9$ +/−10, 20, 30, 40, 50, 60, 70, 80, or 90%) live bacteria of the selected attenuated *Bordetella* strain and any excipient can be separately contained in packaging or in an administration device. The vaccine can be contained within an administration device such as a syringe, spraying device, or insufflator.

Formulations/Dosage/Administration

The compositions described herein can be administered to a mammalian subject (e.g., a human being, a human child or neonate, a human adult, a human being at high risk from developing complications from pertussis, a human being with lung disease, a human being that is or will become immunosuppressed, and a human being having or at high risk for developing respiratory tract inflammation such as asthma, allergic rhinitis, or interstitial lung disease) by any suitable method that deposits the bacteria within the composition in the respiratory tract or other mucosal compartment. For example, the compositions may be administered by inhalation or intranasal introduction, e.g., using an inhaler, a syringe, an insufflator, a spraying device, etc.

The pertactin-deficient *Bordetella* strains described herein can be formulated as compositions for administration to a subject. A suitable number of live bacteria are mixed with a pharmaceutically suitable excipient or carrier such as phosphate buffered saline solutions, distilled water, emulsions such as an oil/water emulsions, various types of wetting agents, sterile solutions and the like. In some cases, the vaccine can be lyophilized and then reconstituted prior to administration. The use of pharmaceutically suitable excipients or carriers which are compatible with mucosal (particularly nasal, bronchial, or lung) administration are preferred for colonizing the respiratory tract. See Remington's Pharmaceutical Sciences, a standard text in this field, and USP/NF.

When formulated for mucosal administration, each dose of a composition can include a sufficient number of live pertactin-deficient *Bordetella* bacteria to result in colonization of the mucosal site, e.g., approximately (i.e., +/−50%) $5 \times 10^3$ to $5 \times 10^9$ bacteria. For administration to human subjects, the dose can include approximately $1 \times 10^6$, $5 \times 10^6$, $1 \times 10$, $5 \times 10^7$, $1 \times 10^8$, $5 \times 10^8$, $1 \times 10^9$, $5 \times 10^9$, or $1 \times 10^{10}$ live pertactin-deficient *Bordetella* bacteria. The dose may be given once or on multiple (2, 3, 4, 5, 6, 7, 8 or more) occasions at intervals of 1, 2, 3, 4, 5, or 6 days or 1, 2, 3, 4, 5, or 6 weeks, or 1, 2, 3, 4, 5, 6, or 12 months. Generally, sufficient amounts of a composition are administered to result in colonization and the protective and/or anti-inflammatory response. Additional amounts are administered after the induced protective and/or anti-inflammatory response wanes (e.g., after the subject resumes suffering from the symptoms of respiratory tract inflammation).

Subjects which can be administered a composition containing live pertactin-deficient *Bordetella* bacteria can include any capable of being colonized with a selected live pertactin-deficient *Bordetella* bacterial strain. For example, the subject can be a mammal such as a human being. Human subjects having, or at high risk of developing, respiratory tract inflammation such as those having or prone to developing allergic asthma or allergic rhinitis are preferred recipients of the composition. While the composition can be used in subjects regardless of their titers of anti-pertactin antibodies, the composition may be used in those having measurable titers (e.g., greater than 10, 20, 50, 100, 200, or 500 ng per ml of serum) of anti-pertactin antibodies and those having previously been immunized with a vaccine containing pertactin or a pertactin-like antigen because pertactin-deficient *Bordetella* bacterial strains are not subject to pertactin-targeting immune responses.

The effectiveness of the compositions in dampening respiratory tract inflammation can be assessed by known methods, e.g., measuring the number of inflammatory cells, IgE titers, levels of pro-inflammatory cytokines/chemokines (such as eotaxin, GM-CSF, IFNγ, IL-4, IL-5, IL-8, IL-10, IL-12, IL-13, IL-17A, IL-17F, IL-18, and TNFα) in fluid taken from the respiratory tract (e.g., bronchoalveolar lavage fluid), or clinical parameters such as spirometry or the level of dyspnea, coughing, wheezing, or respiratory capacity. Improvement in any of one or more of these parameters (at least 10, 20, 30, 40, 50, 60, 70, 80, 90% or more improved compared to a subject not receiving the composition) indicates that the composition is effective. Animal models of allergic respiratory tract inflammation can also be used to assess the effectiveness of a composition, see e.g., U.S. Pat. No. 8,986,709.

EXAMPLES

Example 1—Construction and Characterization of a Pertactin-Deficient Strain of *B. pertussis*

*Escherichia coli* DH5a, SM10 and *B. pertussis* BPZE1, BPSM (Menozzi et al., Infect Immun 1994; 62:769-778) and B1917 (Bart et al. Genome Announc 2014; 2(6)) were used in this study. The *Bordetella* strains were cultured at 37° C. on Bordet-Gengou agar (BG), supplemented with 1% glycerol and 10% defibrinated sheep blood. After growth, the bacteria were harvested by scraping the plates and resuspended in phosphate-buffered saline (PBS) at the desired density. For liquid culture the *Bordetella* strains were grown at 37° C. in modified Stainer-Scholte medium (Imaizuini et al. Infect Immun 1983; 41:1138-1143) containing 1 g/l heptakis (2,6-di-o-methyl) β-cyclodextrin (Sigma). *E. coli* strains used for cloning procedures were growth in LB broth or LB agar plates. When required, streptomycin (Sm) was used at 100 µg/ml, gentamycin (Gm) at 10 µg/ml and ampicillin (Amp) at 100 µg/ml.

Figure 1B:
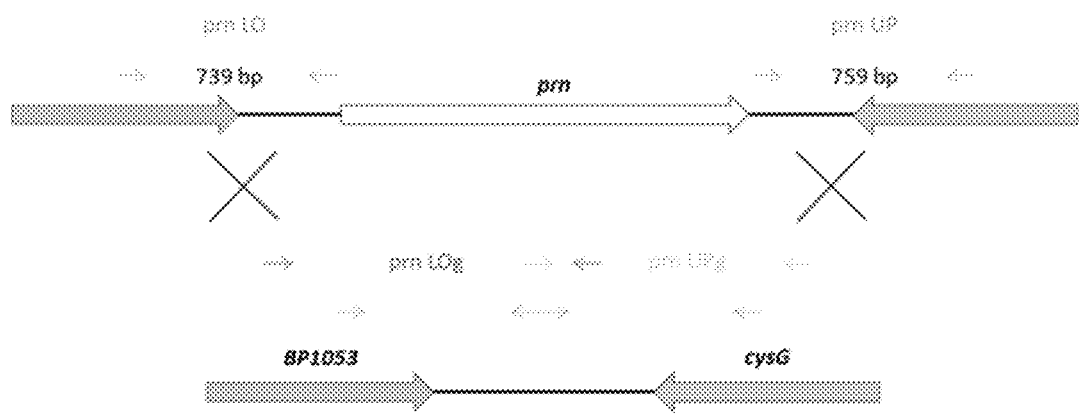
Figure 1B:
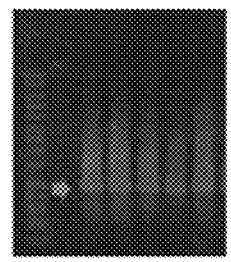
Figure 1B:
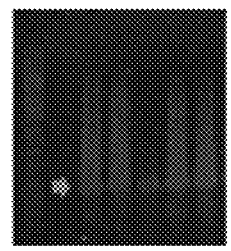

To delete prn, the gene coding for pertactin, in BPZE1, a 739-bp fragment downstream (prn LO) of the prn gene and a 759-bp fragment upstream (prn UP) of the prn gene were cloned into pSS4940 to introduce the prn deletion in the BPZE1 and BPSM genomes by homologous recombination. Referring to FIGS. 1A and 1B, the upstream and downstream prn flanking region were PCR amplified using prn_KO_fw (ATCCTCAAGCAAGACTGCGAGCTG) (SEQ ID NO:1)) and OL_prn_KO_rv (GGGGATAGAC-CCTCCTCGCTTGGATGCCAGGTGGAGAGCA) (SEQ ID NO:2)), and OL_prn_KO_fw (TGCTCTCCACCTG-GCATCCAAGCGAGGAGGGTCTATCCCC) (SEQ ID NO:3)) and prn_KO_ry (CCATCATCCTGTACGAC-CGCCT) (SEQ ID NO:4)), respectively, as primers. These fragments then served as template for a PCR elongation using prn_KO_fw and prn_KO_rv as primers. The resulting fragment (containing the prn deletion) was inserted into the TOPO Blunt® vector (ThermoFisher Scientific) and then excised as a KpnI-NotI fragment. The excised KpnI-NotI fragment was inserted into KpnI- and NotI-digested p554940, a pSS4245 (Inatsuka et al., Infect Immun 2010; 78 2901-2909) derivative. The resulting plasmid was transformed into E. coli SM10, which was then conjugated with BPZE1. Following two successive homologous recombination events, as described elsewhere (Mielcarek et al., PLoS Pathog 2006; 2:e65), referring to FIG. 1B, PCR was used to confirm deletion of the entire prn gene by amplifying the flanking regions covering the construction using prnKO_UP (TTCTTGCGCGAACAGATCAAAC) (SEQ ID NO:5))—prnKOin_UPrv (CTGCTGGTCATCGGCGAAGT) (SEQ ID NO:6)) for the 5' region and prnKO_LOfw (CGCCCAT-TCTTCCCTGTTCC) (SEQ ID NO:7))—prnKO_LO (GAACAGGAACTGGAACAGGCG) (SEQ ID NO:8)) for the 3' region. A strain carrying the prn deletion was selected and named BPZE1P. The same strategy was used to construct a pertactin-deficient BPSM mutant, named BPSMP.

Figure 1C:
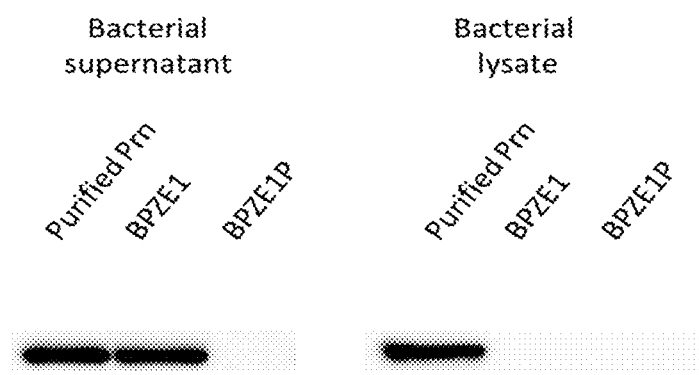

The presence of pertactin was tested by immunoblotting of BPZE1 and BPZE1P lysates and supernatants, using purified Prn (List Biological laboratories) as control for correct size of the band. For protein extraction, BPZE1 and BPZE1P strains were plated onto BG blood agar and incubated for 48 h at 37° C. After growth, the bacteria were scraped off the plates, resuspended in 10 ml of Stainer-Scholte medium and grown for 4 days at 37° C. The bacteria were then harvested by centrifugation. The supernatants were recovered and treated with trichloroacetic acid (TCA) as described previously (Solaris et al., PLoS Pathog 2014; 10:e1004183) for protein concentration. The bacterial pellets were resuspended in PBS complemented with an EDTA-free protease inhibitor cocktail (Roche) and lysed using a French pressure cell. Bacterial debris were removed by centrifugation for 30 minutes at 15,000×g, and the supernatants were recovered for immunoblotting. Proteins were separated by 12% SDS-PAGE and then transferred onto a Nitrocellulose membrane using the Criterion™ cell system (Bio-Rad). After blocking with 5% w/v skim milk powder in PBS 0.01% TWEEN® 20 for 30 min, the membrane was incubated with an anti-pertactin monoclonal antibody pertactin at 1:1,000 dilution. Goat-anti mouse-HRP (Abcam) was then added at a 1:10,000 dilution, and the blot was developed using chemiluminescent substrates (GE Healthcare). As shown in FIG. 1C, an anti-pertactin antibody reactive protein co-migrating with purified pertactin was detected in the supernatant of BPZE1, but not in the supernatant of BPZE1P. This protein was not detected in the bacterial cell lysate of either BPZE1 or BPZE1P.

Example 2—BPZE1P Colonizes Mice as Well as BPZE1

Figure 2:
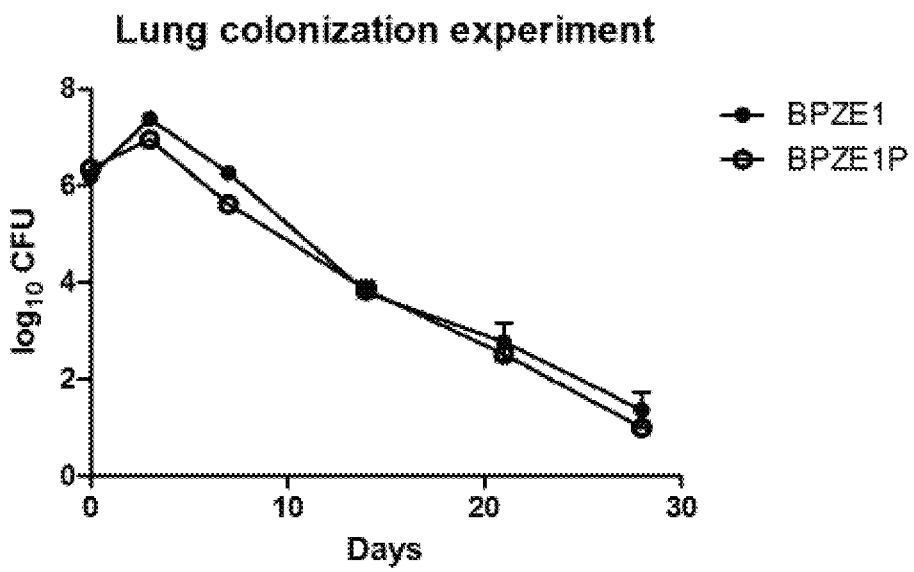
FIG. 2 is a graph showing the results of lung colonization in Balb/c mice using either BPZE1 or BPZE1P.

Groups of 18 six-week old mice were inoculated intranasally with 20 µl PBS containing $10^6$ viable bacteria as described previously (Mielcarek et al., supra). At the indicated time points (3 hours, 3 days, 7 days, 14 days, 21 days and 28 days), 3 mice per group were sacrificed, and lungs were harvested and homogenized for measuring total number of colony formation units (CFU). Statistical analysis was done by a 2-way ANOVA test, using post hoc comparison Bonferroni test with confidence intervals of 95%. Referring to FIG. 2, both BPZE1 and BPZE1P colonized the animals equally well. Both strains exhibited a peak of multiplication 3 days post vaccination and colonization persisted for 4 weeks. No statistically significant difference was observed between these strains in their ability to colonize the mouse lungs.

Example 3—BPZE1P is as Immunogenic and Protective Against Challenge with Virulent B. pertussis as BPZE1

Figure 3:
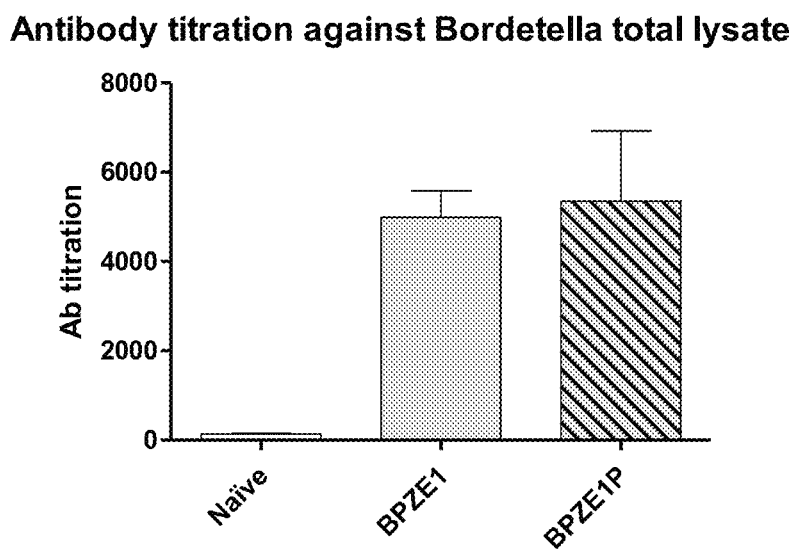
FIG. 3 is a graph showing total IgG titers after BPZE1P or BPZE1 administration to mice.

Immunity induced by BPZE1P in comparison with BPZE1 was measured by antibody titration of mouse immune serum after nasal vaccination. Groups of 8 mice were vaccinated intranasally with $10^5$ viable BPZE1 or BPZE1P. Four weeks later, the mice were bled, and total IgG titers were measured against total BPSM lysate. Blood was centrifuged for 5 min. at 5,000×g to separate the serum from the cells. Antibody titers against B. pertussis were estimated using enzyme-linked immunosorbent assays (ELISA) as described previously (Mielcarek et al., supra), using total B. pertussis BPSM lysate at 1 µg of total protein per well. Statistical analysis was performed using GRAPHPAD PRISM® software. As shown in FIG. 3, BPZE1- and BPZE1P-vaccinated mice exhibited much higher antibody titers than did nave control mice. No significant difference in antibody titers between BPZE1- and BPZE1P-vaccinated mice was detected.

The protective efficacy of BPZE1P compared with BPZE1 was tested in a suboptimal protection protocol by measuring the CFU counts in the lungs 7 days post challenge, and comparing a naïve group with the vaccinated groups. Groups of 8 six-week old mice were vaccinated intranasally with 20 µl PBS containing $10^5$ viable BPZE1 or BPZE1P, or were left unvaccinated. Four weeks later, all mice were challenged intranasally with 20 µl PBS containing $10^6$ viable BPSM, BPSMP or B1917. Three hours after the challenge 3 mice per group were sacrificed, and lungs were harvested and homogenized for CFU counting. The remaining 5 mice per group were sacrificed 7 days after challenge for CFU counting. Three hours post infection, 3 mice were euthanized, and their lungs were harvested to determine the CFU counts shortly after challenge. Seven days post-infection, the remaining 5 mice were euthanized, their lungs were harvested, and the CFU counts were measured. Statistical analysis was done applying a parametric 2-way ANOVA test, using post hoc Bonferroni comparison test with a confidence interval of 95%. *, $p<0.005$; , $p<0.001$; *, $p<0.0001$. As shown in FIGS. 4A-C, vaccination with either strain protected against challenge with BPSM, BPSMP and B1917 equally well. These results show that the deletion of prn does not impact on the protective capacity of the live attenuated vaccine—either against the laboratory strain BPSM, its pertactin-deficient derivative BPSMP, or clinical isolate B1917.

Example 4—BPZE1P Increases Pulmonary Vaccine Uptake in a Pv-Vaccinated Mice

Figure 5:
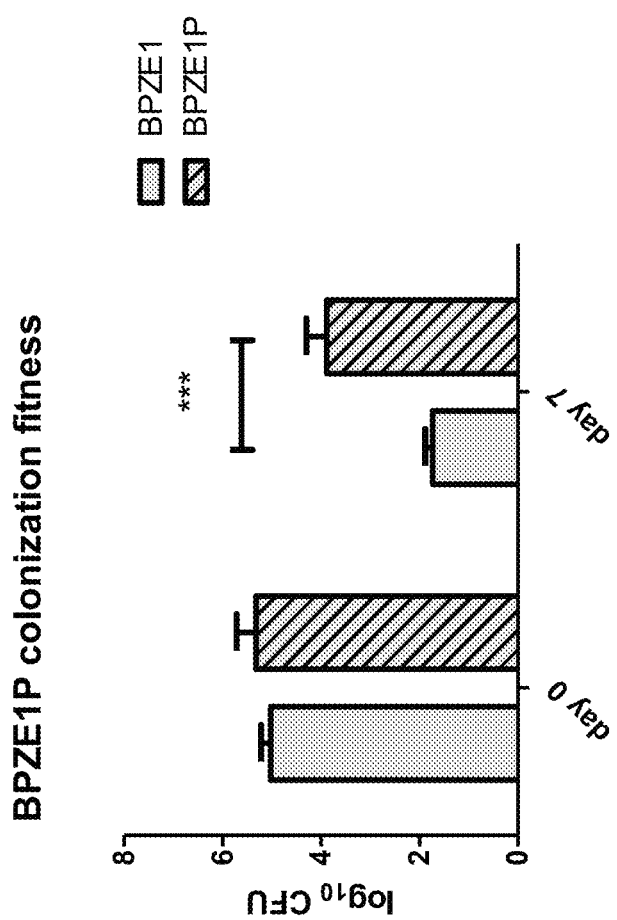
FIG. 5 is a graph showing the fitness of BPZE1 and BPZE1P in mice preimmunized with an acellular *B. pertussis* vaccine (aPv).

The ability of BPZE1P to colonize the lungs of mice having pre-existing antibodies against pertactin was investigated. Groups of 8 six-week old mice were vaccinated subcutaneously with ⅕ of the human dose of the acellular pertussis vaccine (aPv; INFANRIX®, GSK; containing inactivated pertussis toxin, filamentous hemagglutinin and pertactin). Four weeks later, the mice were boosted with the same dose of aPv. Four weeks after boosting, the mice were infected intranasally with $10^6$ BPZE1 or BPZE1P. Three hours post infection, 3 mice were euthanized, and the lungs were harvested to determine the CFU counts. Seven days post-infection, the remaining 5 mice were euthanized, the lungs harvested, and the CFU counts were measured. Statistical analysis was done applying a parametric 2-way ANOVA test, using post hoc Bonferroni comparison test with a confidence interval of 95%. ***, $p<0.0001$. Referring to FIG. 5, at 3 hours post-administration, no significant difference in colonization was seen between the two strains. In contrast, seven days after inoculation, BPZE1P colonized the lungs significantly better than BPZE1. Mice infected with BPZE1P had almost $10^4$ CFU in the lungs 7 days after administration, while the CFU counts in the lungs of the mice given BPZE1 reached $10^2$ CFU. These data show that the deletion of the prn gene improves BPZE1 pulmonary take in mice pre-immunized with pertactin-containing aP vaccine.

Figure 6:
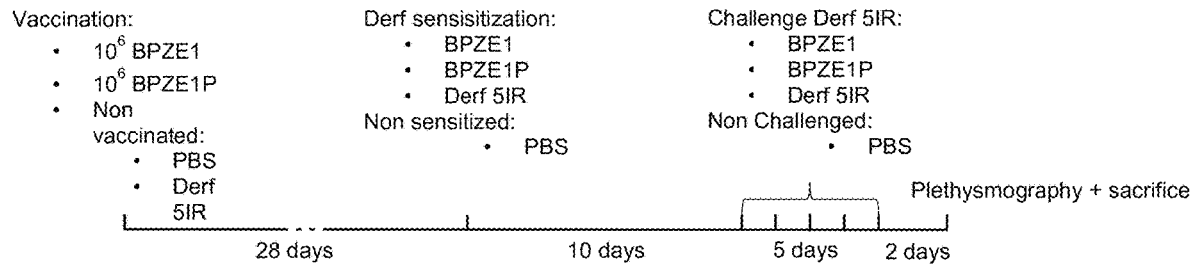
FIG. 6 is a diagram of the experimental protocol of an assay for airway responsiveness in allergic mice vaccinated with BPZE1, BPZE1P or left unvaccinated, and a graph showing the results of the assay.
Figure 6:
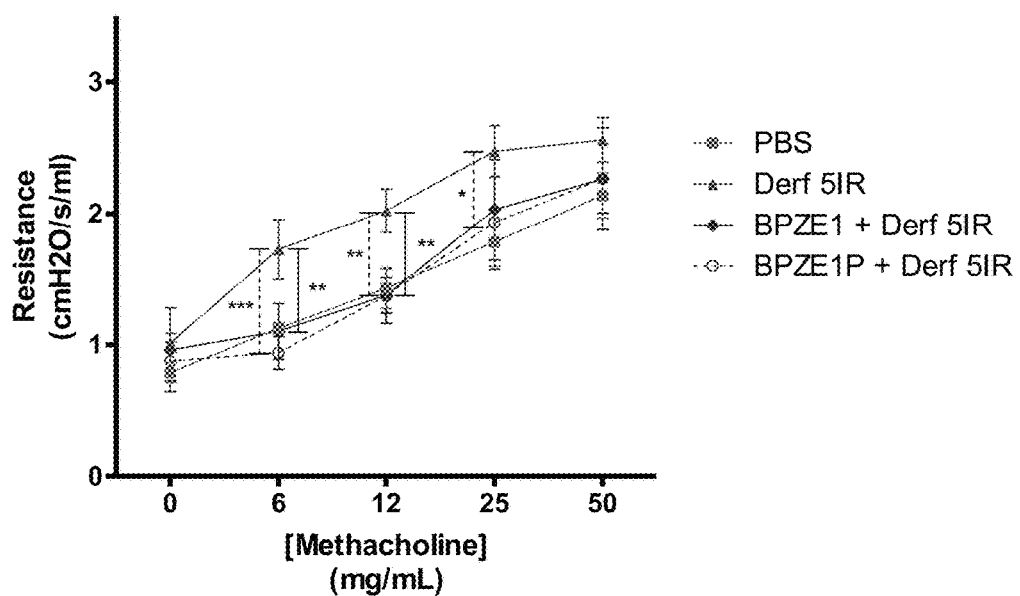

Example 5—BPZE1P and BPZE1 Protect Equally Well Against Allergic Airway Inflammation The effect of vaccination with BPZE1P on airway responsiveness was investigated in allergic mice as described in the protocol shown in FIG. 6. Groups of 4 weeks-old mice were vaccinated intranasally with 20 µl PBS containing $10^6$ viable BPZE1 or BPZE1P, or were left unvaccinated. Four weeks later, the mice were sensitized intranasally with 20 µl of house dust mite (HDM; Stallergenes S.A.) of 5 index of reactivity (IR) of *Dermatophagoides farinae* extract (Derf 5IR) or 20 µl of PBS as control. Ten days later, the mice where challenged intranasally with 20 µl of Derf 5IR or PBS daily for 5 days, and two days later, the mice were anesthetized and intubated intratracheally for mechanical ventilation using the FLEXIVENT® (SCIREQ®) device. The mice were then exposed to increasing concentrations of nebulized methacholine (0-50 mg/mL in PBS) (Sigma-Aldrich) to determine the resistance in their respiratory airways using plethysmography. Statistical analysis was done by applying a parametric 2-way ANOVA test, using the post hoc Bonferroni comparison test with a confidence interval of 95%. *, $p<0.0001$; , $p<0.001$; *, $p<0.005$. In FIG. 6, comparisons between Derf 5IR and BPZE1+Derf 5IR are represented the solid line, and comparisons between Derf 5IR and BPZE1P+Derf 5IR are represented the dashed line. Both the BPZE1- and the BPZE1P-vaccinated mice presented significantly less resistance in their airways after treatment with methacholine at 6, 12 and 25 mg/ml compared to the non-vaccinated mice. The resistance of the vaccinated mice was comparable to that of the PBS control group, which was not sensitized, nor challenged throughout the entire experiment.

Example 6—Measurement of Lung Cell Infiltration and Cytokine Profiles

Figure 7A:
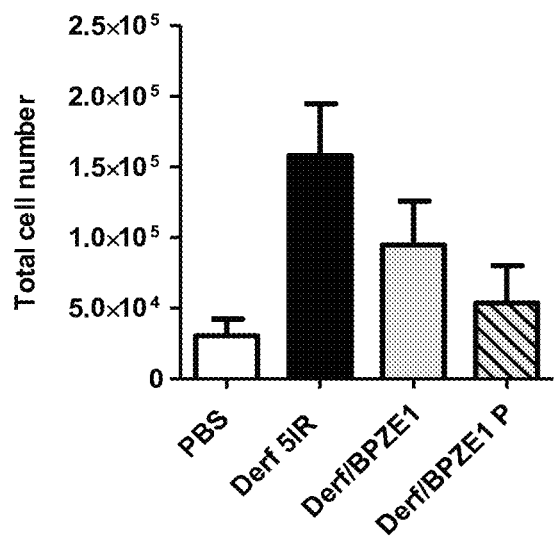
FIG. 7A is a graph showing the total airway cell population infiltration in the bronchoalveolar (BAL) fluid of the allergic mice of the experiments shown in FIG. 6.
Figure 7B:
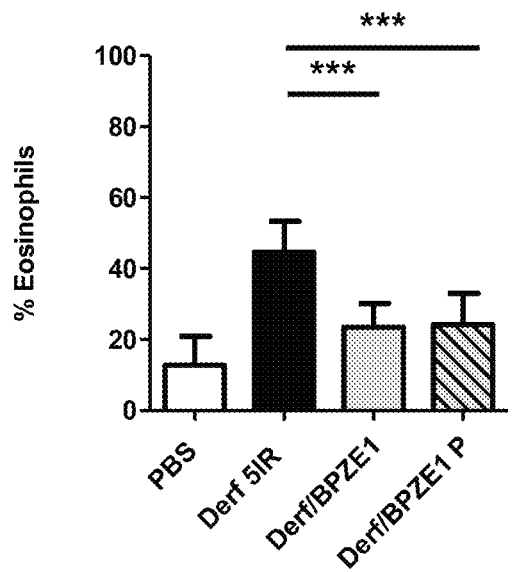
FIG. 7B is a graph showing the percentage of eosinophils in the cells in the BAL fluid of the allergic mice of the experiments shown in FIG. 6.
Figure 7C:
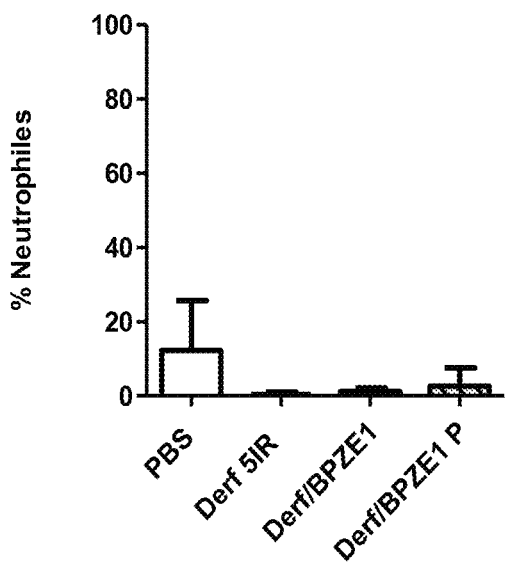
FIG. 7C is a graph showing the percentage of neutrophils in the cells in the BAL fluid of the allergic mice of the experiments shown in FIG. 6.
Figure 7D:
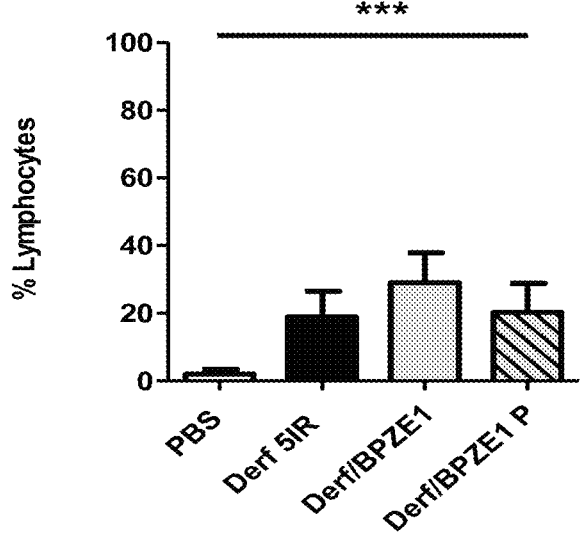
FIG. 7D is a graph showing the percentage of lymphocytes in the cells in the BAL fluid of the allergic mice of the experiments shown in FIG. 6.
Figure 7E:
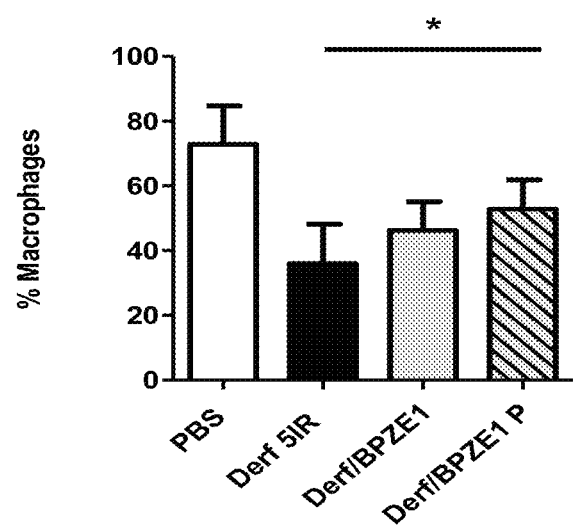
FIG. 7E is a graph showing the percentage of macrophages in the cells in the BAL fluid of the allergic mice of the experiments shown in FIG. 6.
Figure 8A:
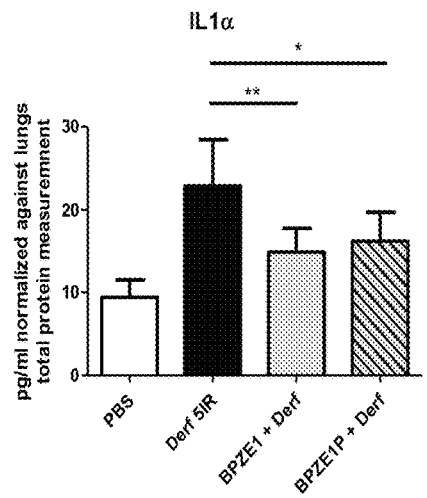
FIG. 8A is a graph showing the amount of IL-1α normalized against total proteins measured in the lung lobe in the allergic mice of the experiments shown in FIG. 6.
Figure 8B:
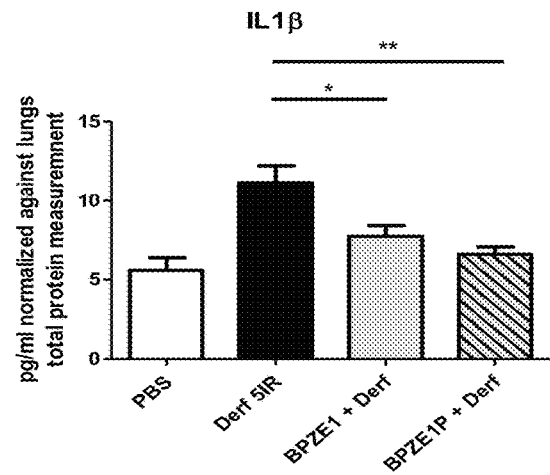
FIG. 8B is a graph showing the amount of IL-1β normalized against total proteins measured in the lung lobe in the allergic mice of the experiments shown in FIG. 6.
Figure 8C:
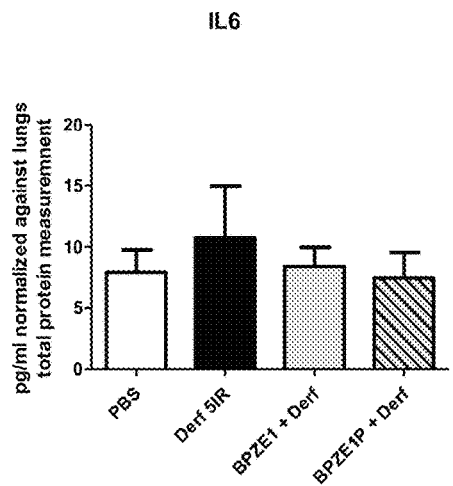
FIG. 8C is a graph showing the amount of IL-6 normalized against total proteins measured in the lung lobe in the allergic mice of the experiments shown in FIG. 6.
Figure 8D:
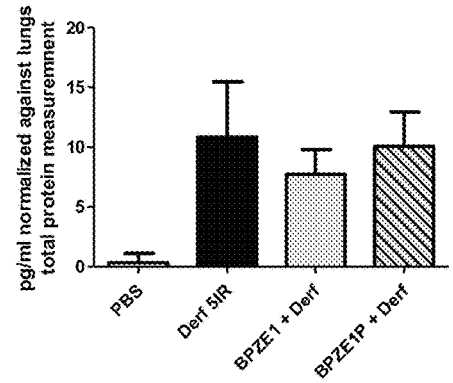
FIG. 8D is a graph showing the amount of IL-13 normalized against total proteins measured in the lung lobe in the allergic mice of the experiments shown in FIG. 6.
Figure 8E:
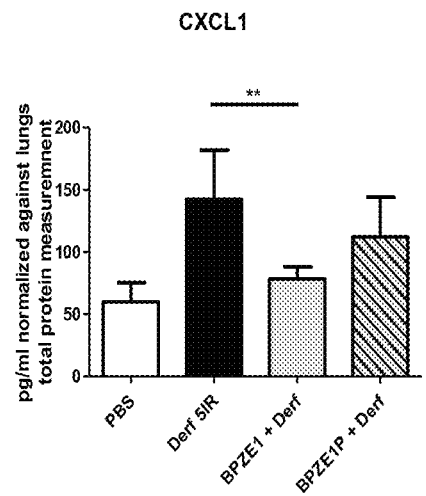
FIG. 8E is a graph showing the amount of CXCL1 normalized against total proteins measured in the lung lobe in the allergic mice of the experiments shown in FIG. 6.
Figure 8F:
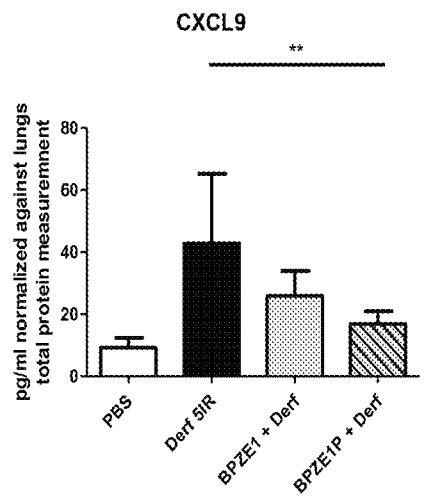
FIG. 8F is a graph showing the amount of CXCL9 normalized against total proteins measured in the lung lobe in the allergic mice of the experiments shown in FIG. 6.
Figure 8G:
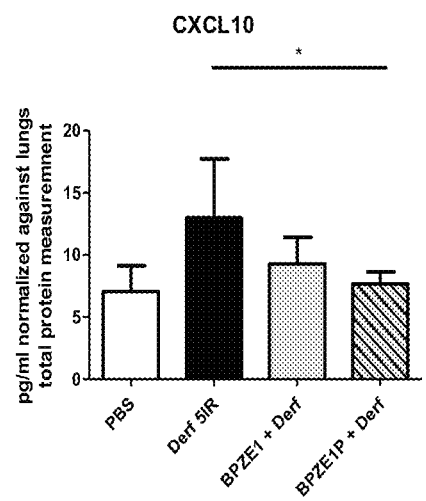
FIG. 8G is a graph showing the amount of CXCL10 normalized against total proteins measured in the lung lobe in the allergic mice of the experiments shown in FIG. 6.
Figure 8H:
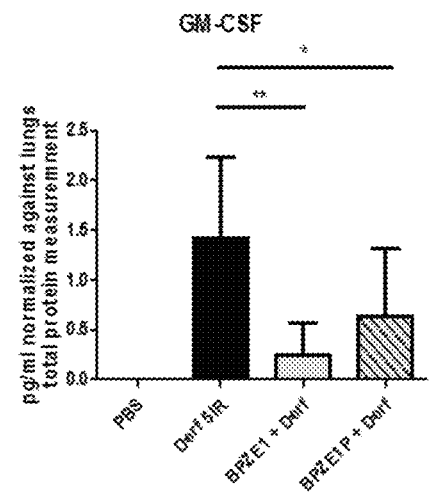
FIG. 8H is a graph showing the amount of GM-CSF normalized against total proteins measured in the lung lobe in the allergic mice of the experiments shown in FIG. 6.

Airway cell population infiltration in the allergic mice of the experiment shown in FIG. 6 and discussed immediately above was assessed. After plethysmography measurements, Bronchoalveolar lavage (BAL) fluids were collected to measure the cell infiltration in the airway. Cells from the BAL fluids were harvested by centrifugation at 1,200 rpm for 5 min at 4° C., resuspended in PBS for cell counting using the Shandon cytospin 4 (Thermo Fisher Scientific) and stained with May Grünwald Giemsa (DiffQuik®) for cell type counting. Total cell numbers were measured in the BAL fluid of mice (FIG. 7A), and percentages of eosinophils (FIG. 7B), neutrophils (FIG. 7C), lymphocytes (FIG. 7D) and macrophages (FIG. 7E) were calculated. Statistical analysis was done by applying a parametric one-way ANOVA test, using the post hoc Bonferroni comparison test with a confidence interval of 95%. ***, $p<0.0001$; *, $p<0.005$. BPZE1 or BPZE1P vaccination significantly reduced the recruitment of total cells in the airways after allergen exposure and challenge, compared to the non-vaccinated mice (FIG. 7A). This reduction reflected essentially the reduction in eosinophil recruitment in the vaccinated mice (FIG. 7B), whereas there was no significant change in the percentages of neutrophils or lymphocytes (FIGS. 7C and D) between the vaccinated and non-vaccinated mice. A small, but significant increase in the percentage of macrophages was observed in the mice that were vaccinated with BPZE1P (FIG. 7E).

Following BAL, the right lung lobes were harvested and directly frozen in liquid Nitrogen for protein extraction. The lung lobes were resuspended in 1 mL of lysis buffer, PBS with 0.5% nonidet P40 and protease inhibitor cocktail (Roche®), and homogenized at 4° C. using T-18 ULTRA-TURRAX® (IKA®). The samples were centrifuged, and the supernatants were collected for total protein quantification using the PIERCE™ BCA protein assay (Thermo Fisher Scientific), and for cytokine and chemokine measurements using the Cytokine 20-Plex Mouse Panel (INVITROGEN™, Thermo Fisher Scientific) per the manufacturer's specifications. Referring to FIG. 8, cytokine levels are represented as the normalization of the cytokine/chemokine quantification against total proteins measured in the lung lobe. Statistical analysis was done by applying a parametric one-way ANOVA test, using the post hoc Bonferroni comparison test with a confidence interval of 95%. **, $p<0.001$. *; $p<0.005$.

As shown in FIG. 8, HDM (Derf 5IR)-treated mice produced significantly increased levels of IL1α and IL1β in the lungs, compared to non-treated mice. Vaccination with BPZE1 or BPZE1P prior to HDM sensitization significantly decreased these levels (FIGS. 8A and B). A similar trend was observed for IL6 and IL13 although the differences between the vaccinated and the non-vaccinated mice did not reach statistical significance (FIGS. 8C and D). Significantly lower levels of induced CXCL1 (KC), CXCL9 (MIG), CXCL10 (IP-10) and GM-CSF were observed in the vaccinated mice compared to the mice which were only treated with HDM (FIG. 8F-H). Generally, there was no statistical difference between the BPZE1-vaccinated and the BPZE1P-vaccinated mice.

Example 7

Figure 9:
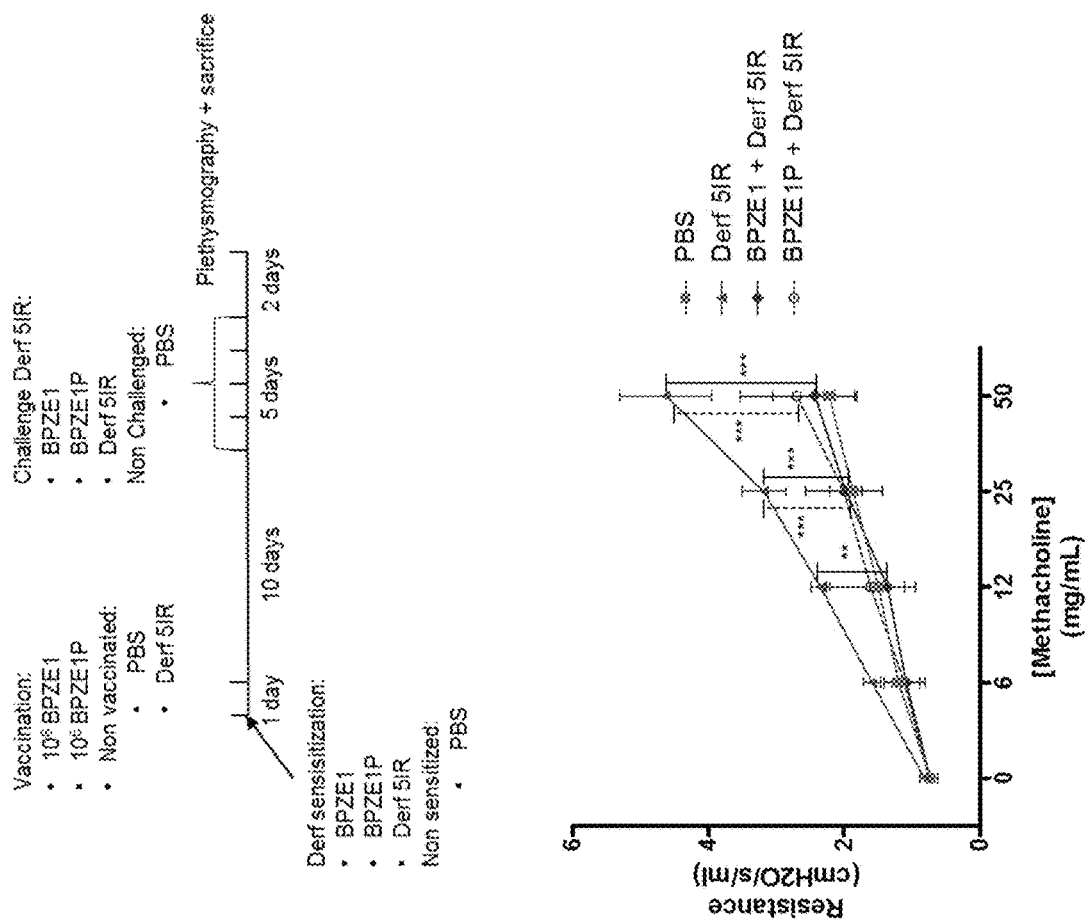
FIG. 9 is a diagram of the experimental protocol of an assay for airway responsiveness in a therapeutic model of allergic mice vaccinated with BPZE1, BPZE1P or left unvaccinated, and a graph showing the results of the assay.

Vaccination of pre-sensitized subjects with either BPZE1 or BPZE1P present significantly lower levels of airway resistance compared to those that were not vaccinated. As shown in the diagram of FIG. 9, groups of 5-week-old mice were either sensitized intranasally with Derf 5IR or administrated PBS, and then either vaccinated with $10^6$ BPZE1 or BPZE1P, or left unvaccinated. Nine days later, the mice were challenged intranasally with Derf 5IR or PBS during 5 days. Two days after last challenge, the mice were anesthetized, and their resistance in the respiratory airway was measured by plethysmography as described above. Statistical analysis was done by applying a parametric 2-way ANOVA test, using the post hoc Bonferroni comparison test with a confidence interval of 95%. *, $p<0.0001$. ; $p<0.001$. Comparisons between Derf 5IR and BPZE1+Derf 5IR are represented by the solid line, and comparisons between Derf 5IR and BPZE1P+Derf 5IR are represented by the dashed line. The mice vaccinated with either BPZE1 or BPZE1P present significantly lower levels of airway resistance compared to those that were not vaccinated. Again, the airway resistance of the vaccinated mice was indistinguishable from that of the control group, which were not sensitized nor challenged with Derf 5IR.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing or preventing the development of allergic airway inflammation in a subject sensitized to an allergen, the method comprising the step of administering to the respiratory tract of the subject an amount of a composition comprising a pharmaceutically acceptable carrier and live attenuated *Bordetella pertussis* sufficient to colonize the respiratory tract of the subject, wherein the colonization of the respiratory tract of the subject results in the reduction or the prevention of the development of airway inflammation in the subject compared to the level of airway inflammation in a corresponding subject not sensitized to the allergen and not administered with the composition, and wherein the live attenuated *Bordetella pertussis* are deficient in pertactin, tracheal cytotoxin (TCT), pertussis toxin (PTX), and dermonecrotic toxin (DNT).

2. The method of claim 1, wherein the airway inflammation is characterized by airway resistance, and the colonization of the respiratory tract of the subject administered with the composition results in the reduction or the prevention of the development of airway resistance.

3. The method of claim 1, wherein the airway inflammation is characterized by eosinophil infiltration in the lungs of the subject, and the colonization of the respiratory tract of the subject administered with the composition results in reduction or prevention of the eosinophil infiltration.

4. The method of claim 1, wherein the airway inflammation is characterized by development of increased amounts of inflammatory cytokines in the lungs of the subject administered with the composition, and the colonization of the respiratory tract of the subject administered with the composition results in reduction or prevention of the development of the increased amounts of the inflammatory cytokines.

5. The method of claim 1, wherein the live attenuated *Bordetella pertussis* lack a functional gene encoding the pertactin.

6. The method of claim 1, wherein the live attenuated *Bordetella pertussis* are of the BPZE1P strain deposited with the Collection Nationale de Cultures de Microorganismes under the accession number CNCM-I-5150.

7. The method of claim 1, wherein the subject administered with the composition has interstitial lung disease.

8. The method of claim 1, wherein the subject administered with the composition has asthma.

9. The method of claim 1, wherein the subject administered with the composition has allergic rhinitis.

10. The method of claim 1, wherein the subject has previously been immunized with a vaccine containing a pertactin antigen.

11. The method of claim 1, wherein the subject has greater than 10 nanogram per ml of serum antibodies to *Bordetella pertussis* pertactin.

* * * * *

```
                       SEQUENCE LISTING

<160> NUMBER OF SEQ ID NOS: 8

<210> SEQ ID NO 1
   <211> LENGTH: 24
   <212> TYPE: DNA
   <213> ORGANISM: Artificial Sequence
   <220> FEATURE:
   <223> OTHER INFORMATION: Description of Artificial Sequence: Synthetic
         primer

<400> SEQUENCE: 1
atcctcaagc aagactgcga gctg                                          24

<210> SEQ ID NO 2
   <211> LENGTH: 40
   <212> TYPE: DNA
   <213> ORGANISM: Artificial Sequence
   <220> FEATURE:
   <223> OTHER INFORMATION: Description of Artificial Sequence: Synthetic
         primer

<400> SEQUENCE: 2
ggggatagac cctcctcgct tggatgccag gtggagagca                         40

<210> SEQ ID NO 3
   <211> LENGTH: 40
   <212> TYPE: DNA
   <213> ORGANISM: Artificial Sequence
   <220> FEATURE:
   <223> OTHER INFORMATION: Description of Artificial Sequence: Synthetic
         primer

<400> SEQUENCE: 3
tgctctccac ctggcatcca agcgaggagg gtctatcccc                         40

<210> SEQ ID NO 4
   <211> LENGTH: 22
   <212> TYPE: DNA
   <213> ORGANISM: Artificial Sequence
   <220> FEATURE:
   <223> OTHER INFORMATION: Description of Artificial Sequence: Synthetic
         primer

<400> SEQUENCE: 4
ccatcatcct gtacgaccgc ct                                            22

<210> SEQ ID NO 5
   <211> LENGTH: 22
   <212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 5
ttcttgcgcg aacagatcaa ac                                              22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctgctggtca tcggcgaagt                                                 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgcccattct tccctgttcc                                                 20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gaacaggaac tggaacaggc g                                               21
```